United States Patent [19]

McRae

[11] Patent Number: Plant 6,696

[45] Date of Patent: Mar. 28, 1989

[54] HYBRID LILY PLANT NAMED STAR PIXIE

[75] Inventor: Edward A. McRae, Boring, Oreg.

[73] Assignee: Melridge, Inc., Gresham, Oreg.

[21] Appl. No.: 101,491

[22] Filed: Sep. 28, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers of excellent form and comparatively large size particularly characterized by their rich orange coloration, accented by a golden orange midrib, the plant itself being of medium height with abundant foliage. This moderately short stature and the large clusters of flowers make this plant especially suitable as a pot plant variety, its color pattern and silhouette being completely new in the upright Asiatic divisions of lilies suited to forcing and to mass commercial cultivation. The plant is highly resistant to disease and shows high tolerance of virus. It is an excellent garden plant and the bulb may be precooled and forced throughout the year for pot plant production.

1 Drawing Sheet

BACKGROUND OF THE INVENTION

This new variety of lily plant originated as a seedling selected from a group of seedlings planted by me at Sandy, Oreg., with seeds derived from a hybrid resulting from my using the clonal cultivar 'Charisma' (U.S. Plant Pat. No. 4,180) as the seed parent and the clonal cultivar 'Sunray' as the pollen parent. My objective for this crossing was the production of lilies having colors in the shades of orange and yellow well suited to forcing for pot plant production out-of-season and the present seedling was selected for asexual reproduction because it appeared to have the desirable characteristics of medium to large size, the rich orange coloration of its flowers accented by golden orange midribs, and an attractive "ring" of spots in the center of the flowers, a feature unique in this type lily. Asexual reproduction of this selected seedling was done by me and under my direction at Sandy, Oreg., by bulb scale propagation with results that appeared so satisfactory that further reproduction was done under by direction at Sandy, Oreg., through several successive generations by bulb scale propagation as well as by natural propagation from bulblets and this work has demonstrated clearly that the novel and distinctive characteristics of this new lily variety are fixed and hold true, under asexual propagation, from generation to generation.

Work with this new variety shows that it remains relatively short and is not overly susceptible to bud abortion when forced into flower out-of-season as a pot plant. In addition, it possesses all of the desired characteristics of excellence of form and habit and the clone is vigorous and a good grower and propagator, as observed at Sandy, Oreg.

This new plant is well suited to forcing out-of-season when the bulbs are dug at the appropriate time and properly precooled. For example, October-dug bulbs, properly precooled and potted in January, will flower under glass at western Oregon in an average of sixty-five to seventy-five days, with no supplemental lighting and at moderate greenhouse temperatures.

DESCRIPTION OF THE DRAWING

My new variety of lily plant is illustrated by the accompanying photographic drawing which shows the open bloom in full color and illustrates the flower form, the tepal arrangement, and the novel and distinctive rich orange coloration with the golden orange midrib, the colors shown being as nearly true to those herein specified as is reasonably possible to obtain by professional photographic procedures.

DESCRIPTION OF THE NEW VARIETY

The following is a detailed description of my new variety of Asiatic hybrid lily with nomenclature according to The International Lily Register, Second Edition, published in 1969 by the The Royal Horticultural Society of London, England, and with color designations according to The R.H.S. Colour Chart published by the society in 1966.

THE PLANT

Origin: Seedling.

Parentage:

*Seed parent.*—Lilium 'Charisma' (U.S. Plant Pat. No. 4,180).

*Pollen parent.*—Lilium 'Sunray'.

Classification:

*Horticultural.*—Division I-A, Upright Asiatic Hybrid Lily, according to The Horticultural Classification of Lilies, by The Royal Horticultural Society of London.

*Commercial.*—Hybrid Lilium Clone.

Form: Single stem, erect and stately.

Height: About 50 to 65 cm. on stems profuded by glasshouse forcing of bulbs of about 15 to 18 cm. in circumference; provided that their light levels are adequate; low light levels may cause "stretching".

Growth: Vigorous and upright.

Foliage:

*Quantity.*—Abundant.

*Leaf size.*—About 6 to 12 cm. long and about 1 cm. wide.

*Leaf shape.*—Lanceolate with acuminate tip.

*Texture.*—Leathery.

*Aspect.*—Glossy, the upper leaves having pubescent margins.

*Color.*—Dark green on upper side and somewhat lighter green on the lower side.

The bulbs:

*Size.*—Various, ranging to about 25 cm. in circumference in commercial use.

*Color.*—White.

THE BUD

Form: Long ovoid with obtuse apex.

Size: About 8 to 9 cm. long and about 6 to 7 cm. in circumference just prior to opening.

Opening rate: The bud opens slowly, taking about one hour in response to morning light.

Color: Buff Orange, R.H.S. 30 D, overlayed with soft green along the midrib just prior to opening and as the tepals begin to unfurl, the bud being noticeably pubescent.

Peduncle:

*Length.*—Averages about 4 to 8 cm., but may elongate if light levels are too low or if bulbs have been improperly stored prior to forcing.

*Color.*—Deep green with soft plum overlay.

THE FLOWER

Blooming habit: Once annually and profusely in midseason.

Size: Large. The flowers average about 14 to 17 cm. in diameter.

Borne: As a single compact raceme inflorescence producing five to eight buds from a bulb of about 12 to 16 cm. in circumference.

Shape: Cup-shaped upon first opening and flattening as the tepals recurve by the second day.

Tepalage:

*Number.*—Six in hexagonal arrangement with the inner tepals alternating between the outer tepals.

*Size.*—Inner tepals average about 4 to 4.5 cm. wide and the outer tepals average about 3 cm. wide.

*Color.*—The base color is a rich Orange, R.H.S. 30 A, and there is a band of Golden Orange, R.H.S. 24 A, about 1 m. wide extending about 4 cm. from the nectaries along the midrib of each tepal. The nectaries are soft orange but they are covered with short, white pubescence.

*Shape.*—Obovate with acuminate tip and the outer tepals have lightly frilled margins.

*Apperance.*—The tepals are shiny.

*Spotting.*—The basal third of the inner tepals only is marked with about five to twenty small magenta-purple spots just about the nectary, the tepal spotting collectively forming a "ring" of spots encircling the center of the flower.

*Tepal longevity.*—The tepals stay on the stem about three weeks.

*Color changes.*—The flower color deepens to Orange-Red, R.H.S. 30 B-C, as the flower ages, if the light levels are adequate for cut flower and pot plant maintenance.

Pedicel:

*Length.*—Averages about 5 to 10 cm.

*Color.*—Dark green with light plum overlay.

*Character.*—Sturdy and ascending up to about 60° from the horizontal; very rarely having secondary buds.

Fragrance: None.

Disease resistance: The flower and plant are resistant to disease. In particular they are resistant to Fusarium Bulb Rot and Botrytis Blight, as observed in western Oregon.

Lasting quality: The flower is long lasting, both on the plant and as a cut flower.

THE REPRODUCTIVE ORGANS

Stamens:

*Number.*—Six.

*Arrangement.*—Typical of genus Lilium.

*Anthers (Dehisced).*—Color: R.H.S. Greyed Orange, R.H.S. 169 A.

*Filments.*—Length: About 5 cm. Color: Orange-Red, R.H.S. 28 B-C.

Pistil:

*Number.*—One.

*Length.*—About 5 cm.

*Stigma.*—Color: Greyed Red, R.H.S. 180 A-B, with plum overlay.

The ovary: The ovary is characteristic of that of the genus Lilium.

THE FRUIT

Fertility: The fruit is fertile.

Shape: Ovoid.

Color at maturity: Soft brown, sometimes overlaid with soft plum.

This new lily variety most closely resembles 'Irish Pixie' but has slightly larger and more deeply colored flowers with a longer golden orange "ray" on each tepal. The new plant is slightly taller than 'Irish Pixie' and has flowers with only the inner tepals bearing any spots. The new plant has slightly lighter colored stems than 'Irish Pixie', has longer leaves, and has more pubescent buds and upper leaves.

I claim:

1. The new and distinctive variety of Asiatic hybrid lily plant and parts thereof, substantially as herein shown and described, characterized by its large, rich orange flowers accented by lighter colored orange midribs, and by its relatively short stemmed, full leaved, upright flowering silhouette.

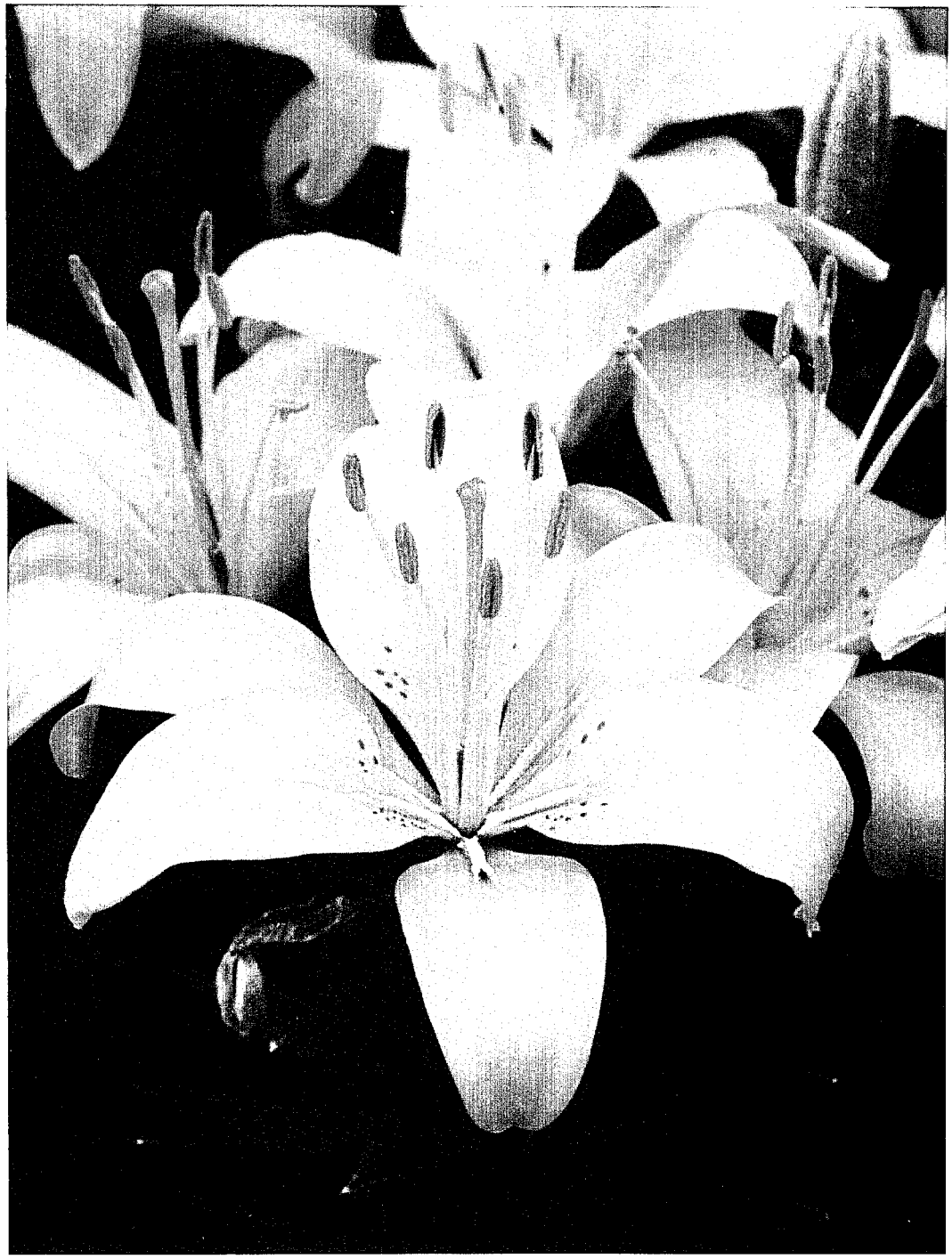

* * * * *